United States Patent
Eisenbarth et al.

(10) Patent No.: US 7,145,000 B2
(45) Date of Patent: Dec. 5, 2006

(54) MARKABLE COMPOUNDS FOR EASY SYNTHESIS OF 3'-[$^{18}$F] FLUORO-3'-DEOXYNUCLEOTIDES, AND METHOD FOR THEIR PRODUCTION

(75) Inventors: Joseph Antonius Maria Eisenbarth, Ketsch (DE); Stefan Johannes Martin, Dossenheim (DE); Ulrike Wagner-Utermann, Heppenheim (DE); Michael Eisenhut, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 86 days.

(21) Appl. No.: 10/487,480

(22) PCT Filed: Aug. 21, 2002

(86) PCT No.: PCT/EP02/09361

§ 371 (c)(1),
(2), (4) Date: Jun. 28, 2004

(87) PCT Pub. No.: WO03/018599

PCT Pub. Date: Mar. 6, 2003

(65) Prior Publication Data

US 2005/0143338 A1    Jun. 30, 2005

(30) Foreign Application Priority Data

Aug. 23, 2001 (DE) ............... 101 41 300

(51) Int. Cl.
C07H 19/00  (2006.01)
C07H 19/048  (2006.01)
C07H 19/06  (2006.01)

(52) U.S. Cl. .............. 536/28.1; 536/28.4; 536/28.5
(58) Field of Classification Search ............... 536/28.1, 536/28.4, 28.5; 514/42, 43, 49, 50
See application file for complete search history.

(56) References Cited

OTHER PUBLICATIONS

Minamoto et al., "Synthesis and Alkali-Hydrolysis Reactions of some 2,3'-(Substituted imino)pyrimidine Nucleosides Lacking a 2'-Hydroxyl Group", J. Org. Chem., vol. 54, pp. 4543-4549, 1989.*
Doerr et al., "The Introduction of a 2,3'-Imino Bridge into Pyrimidine Nucleosides", Journal of the American Chemical Society, 89;7, pp. 1760-61, 1967.*
Doerr et al., "Synthesis of 2,3'-Imino-1-(2-deoxy-β-D-threo-pentofuranosyl)thymine and related derivatives", Journal of Organic Chemistry, vol. 33, No. 4, pp. 1592-1599, 1968.*
Minamoti et al., "Synthesis and Alkali-Hydrolysis Reactions of Some 2,3'-(Substituted imino) pyrimidine Nucleosides Lacking a 2'-Hydroxyl Group," Journal of Organic Chemistry, vol. 54, No. 19, pp. 4543-4549, 1989.
Grierson et al., "Radiosynthsis of 3'-Deoxy-3'-[$^{18}$F]fluorothymidine: [$^{18}$F]FLT for Imaging of Cellular Proliferation In Vivo," Nuclear Medicine & Biology, vol. 27, pp. 143-156, 2000.
Machulla et al., "Simplified labeling approach for synthesizing 3'-deoxy-3'-[$^{18}$F]fluorothymidine ([$^{18}$F]FLT)," Journal of Radioanalytical and Nuclear Chemistry, Fol. 243, No. 3, pp. 843-846, 2000.
Wodarski et al., "Synthesis of 3'-Deoxy-3'-[$^{18}$F]Fluoro-Thymidine with 2,3'-Anhydro-5'-0-(4,4'-Dimethoxytrityl)-Thymidine," Journal of Labelled Compounds and Radiopharmaceuticals, vol. 43, pp. 1211-1218, 2000.

* cited by examiner

Primary Examiner—James O. Wilson
Assistant Examiner—Traviss C. McIntosh III
(74) Attorney, Agent, or Firm—Patterson, Thuente, Skaar & Christensen, P.A.

(57) ABSTRACT

What is described are compounds

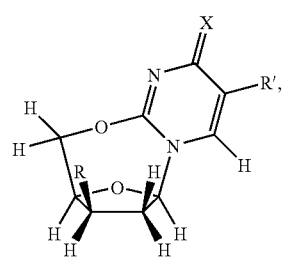

(1)

wherein R represents Br, I or $R^1$—$SO_3$, where $R^1$ is an unsubstituted or substituted $C_1$–$C_5$-alkyl group, or an unsubstituted or substituted phenyl group;
X is O or NR", where R" is a usual protective group for N; and
R' represents hydrogen, a halogen, such as F, Cl, and Br, a substituted or unsubstituted $C_1$–$C_7$-alkyl group, such as methyl and ethyl, a substituted or unsubstituted $C_2$–$C_7$-alkenyl group, or a substituted or unsubstituted $C_2$–$C_7$-alkynyl group.

9 Claims, No Drawings

MARKABLE COMPOUNDS FOR EASY SYNTHESIS OF 3'-[$^{18}$F] FLUORO-3'-DEOXYNUCLEOTIDES, AND METHOD FOR THEIR PRODUCTION

The invention relates to compounds that are suitable as markable precursor substances for the production of 3'-[$^{18}$F] fluoro-3'-deoxynucleotides, in particular, a method for their production, and the use thereof in the synthesis of 3'-[$^{18}$F] fluoro-3'-deoxynucleotides, in particular.

In nuclear medicine, the method known as positron emission tomography (PET) can be used to study the modes of action of the body's own substances or foreign substances, such as drugs, as well as metabolic processes in the brain and other organs, especially tumors. PET is used especially often in tumor diagnostics. To this end, biologically relevant compounds marked with positron-emitting radionuclides are injected and the emitted γ radiation is recorded in tomograms. 3'-Deoxynucleotides that feature a positron-emitting radionuclide, such as $^{18}$F, in the 3' position can be used as marked compounds in this process.

An example of such a marked compound is 3'-[$^{18}$F] fluoro-3'-deoxythymidine ([$^{18}$F]FLT),

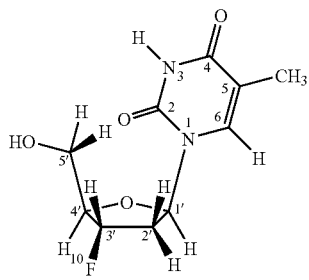

which accumulates in rapidly dividing cells, such as those that are present in tumors. In this manner, tumors, especially in the brain but also in the torso, can be located or, as an adjunct to therapy, a response to a treatment can be evaluated or optimized.

Currently, the production of [$^{18}$F]FLT passes through several intermediate stages, during which highly toxic chemicals are used or created, which must be completely removed prior to administration of the proliferation marker [$^{18}$F]FLT, so that they do not harm the subject being examined.

Grierson, J. R. and Shields, A. F., in *Nucl. Med. Biol.* 2000, 27, 143–156, describe a complex synthesis of marking precursors for the production of [$^{18}$F]FLT, in which some highly toxic compounds, such as phosgene, are used. This process involves the use of dimethoxybenzyl-N protective groups, which must be oxidatively split off with Cer(IV) ammonium nitrate. However, Cer compounds are highly toxic, and for this reason must be quantitatively removed in a reproducible precipitation reaction. Although these procedures are generally performed manually, this should be avoided for reasons of protection against radiation, because radiation loads and the risk of contamination of human beings should be kept as low as possible.

Machulla et al., in *J. Radioanal. Nucl. Chem.*, 2000, 243, 843–846, and Wodarski et al., in *J. Labelled Cpd. Radiopharm.*, 2000, 43, 1211–1218, describe the synthesis of marking precursors for the production of [$^{18}$F]FLT in processes in which, however, extreme reaction conditions such as reaction temperatures of about 160° C. are applied and DMSO is used as a solvent. This limits or even precludes application of the synthesis to commercially obtainable synthesis modules. Furthermore, DMSO, as a high boiling point solvent, is very difficult to extract.

SUMMARY OF THE INVENTION

In the first aspect, this invention features a compound of the following formula:

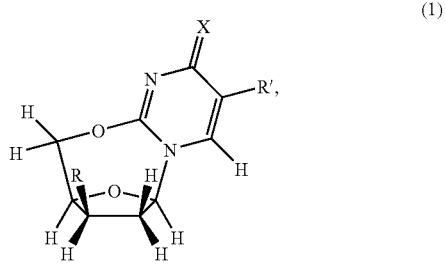

wherein R represents Br, I or $R^1$—$SO_3$, wherein $R^1$ is an unsubstituted or substituted $C_1$-$C_5$-alkyl group, or an unsubstituted or substituted phenyl group; X is O or NR", wherein R" is a usual protective group for N; and R' represents hydrogen, halogen, such as F, Cl or Br, a respectively substituted or unsubstituted $C_1$-$C_7$-alkyl group, a respectively substituted or unsubstituted $C_2$-$C_7$-alkenyl group, or a respectively substituted or unsubstituted $C_2$-$C_7$-alkynyl group.

In the second aspect, this invention features a method for producing the compound of claim 1 comprising the step of introducing a radical R into a second compound having the following formula:

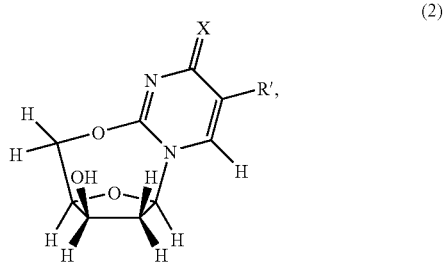

wherein R is Br, I, or a $R^1$—$SO_3$ group where $R^1$ is an unsubstituted or substituted $C_1$-$C_5$-alkyl group or an unsubstituted or substituted phenyl group;

X is O or a NR" group, where R" is a usual protective group for N; and

R' is hydrogen, a halogen, a substituted or unsubstituted $C_1$-$C_7$-alkyl group, a substituted or unsubstituted $C_2$-$C_7$-alkenyl group, or a substituted or unsubstituted $C_2$-$C_7$-alkynyl.

In the third aspect, this invention features a method of making 3'-[$^{18}$F] fluoro-3'-deoxythymidine comprising the step of inserting a nucleophile at the 3' position of the compound of claim 1.

DETAILED DESCRIPTION OF THE INVENTION

Thus, the goal of this invention is to provide a markable compound for the synthesis of 3'-deoxynucleotides, which feature a positron-emitting radionuclide, such as $^{18}F$, in the 3' position, but not the disadvantages known in the art.

According to the invention, this goal is attained with a compound characterized by the fact that it has a structure of formula (1):

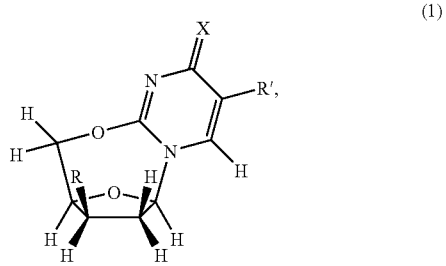

(1)

wherein R represents Br, I or $R^1$—$SO_3$, where $R^1$ is an unsubstituted or substituted $C_1$–$C_5$-alkyl group, or an unsubstituted or substituted phenyl group;

X is O or NR", where R" is a usual protective group for N; and

R' represents hydrogen, a halogen, such as F, Cl, and Br, a respectively substituted or unsubstituted $C_1$–$C_7$-alkyl group, such as methyl and ethyl, a respectively substituted or unsubstituted $C_2$–$C_7$-alkenyl group, or a respectively substituted or unsubstituted $C_2$–$C_7$-alkynyl group.

"Usual protective groups" within the meaning of this invention are those organic radicals with which amino functions can be temporarily protected against attack by reagents. The person skilled in the art is familiar with such usual protective groups for amino functions, which include, for example, the benzyloxycarbonyl, the tert-butoxycarbonyl, the 9-fluorenylmethoxycarbonyl, the triphenylmethyl or the nitrobenzolsulfenyl group.

The substituents present at the $C_1$–$C_7$-alkyl, $C_2$–$C_7$-alkenyl, or $C_2$–$C_7$-alkenyl can be halogens, such as F, Cl, Br, $NO_2$, $Ph_3Sn$, $Bu_3Sn$, $Me_3Sn$, $Ph_3Si$, $Bu_3Si$ and/or $Me_3Si$.

According to the above formula (1), R represents $R^1$—$SO_3$, wherein $R^1$ can be an unsubstituted or substituted $C_1$–$C_5$-alkyl. An example of an unsubstituted $C_1$–$C_5$-alkyl is methyl, i.e., $R^1$—$SO_3$ comprises methane sulfonyl. These are favorable, because the reaction in which they can be inserted into the compound of the invention, such as mesylation, takes place quickly and high yields of the compound of the invention are obtained.

The substituent on the $C_1$–$C_5$-alkyl is preferably an electron-drawing group, so that the radical R represents a good leaving group. Examples of electron-withdrawing groups are halogens, such as F, Cl, Br and I, as well as $NO_2$, wherein fluorine is especially well-suited, because of its favorable electron-drawing properties. In the substituted $C_1$–$C_5$-alkyl, 1 H atom up to all of the H atoms of the alkyl radical can be replaced with an electron-withdrawing substituent, which can be selected independently of one another. An especially preferred representative of the substituted $C_1$–$C_5$-alkyl radical is $CF_3$, i.e., $R^1$—$SO_3$ comprises trifluoromethane sulfonyl, which is an especially favorable leaving group.

As already explained above, the radical $R^1$ can be an unsubstituted or substituted phenyl. This phenyl can have 1 [one] or more substituents, which can be identical or different. The substituents can be located in the o, m and/or p position relative to the $SO_3$ radical. Examples of suitable substituents are $C_1$–$C_5$-alkyl radicals, such as methyl, or electron-drawing groups, especially halogens, such as F, Cl, Br and I, as well as the $NO_2$ group, which results in the radical R representing a favorable waste group. Preferred radicals $R^1$—$SO_3$ with substituted phenyl comprise 4-nitrophenylsulfonyl or p-toluene sulfonyl, which are especially favorable waste groups.

Especially preferred compounds of the invention are 1-(3'-O-mesyl-2,5'-anhydro-β-D-lyxofuranosyl)-thymine, 1-(3'-O-mesyl-2,5'-anhydro-β-D-lyxofuonosyl)-uridine and 1-(3'-O-mesyl-2,5'-anhydro-β-D-lyxofuranosyl)-cytidine.

Surprisingly, it has now been discovered that the compound [$^{18}F$]FLT used in positron emission tomography or another 3'-deoxynucleotide marked at the 3' position with a positron-emitting radionuclide can be easily and quickly produced beginning with the compounds of the invention. The compounds of the invention serve as precursor substances for the synthesis of proliferation markers, such as [$^{18}F$]FLT, which, as a result of intramolecular protection of non-derivative functional groups (5'-O and 3-N position) during hydrolysis into the target molecule, such as [$^{18}F$]FLT, do not release any toxic products from the separation of the protective groups. This facilitates the preparation of the reaction solution and validation of the synthesis process into a GMP/GLP-compliant, applicable radiopharmacon. Radiomarking into [$^{18}F$]FLT, for example, is simple, fast and produces good yields at a high degree of purity and under mild conditions.

The anhydro structure used in the compounds of the invention replaces the otherwise necessary use of protective groups in the $N^3$ and 5' positions. The intramolecular protection of those functional groups that are not to be derived has not yet been described in this configuration. This intramolecular protection completely prevents the development of split-off protective group products during alkaline hydrolysis of the anhydro structure, which, in previous methods, developed in equimolar substance quantities during hydrolysis of the precursor compound.

The subject matter of this invention is also a method for producing the inventive compound of formula (1), wherein, in a compound of formula (2)

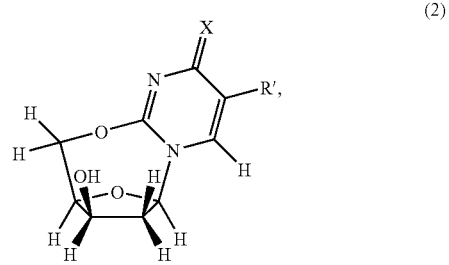

(2)

in which X and R' are defined as above, the radical R is introduced, wherein R is as defined above.

Depending on the chemical nature of R, the introduction of R can occur in a manner known in the art. Such methods are known to the person skilled in the art, who is familiar with the necessary reaction conditions, chemicals and equipment.

For example, $R^1$—$SO_2$ can be introduced into the compound of the invention by allowing the compound (2) to react with R¹—SO₂Hal, wherein R¹ is defined as above and Hal represents a halogen, especially chlorine. Examples of R¹—SO₂Hal are methane sulfonyl chloride, 4-nitrophenyl sulfonyl chloride, p-toluene sulfonyl chloride and trifluoromethane sulfonic acid chloride. This reaction can be performed in an advantageous manner at moderate temperature. Dry pyridine or a dry mixture of triethylamine/dichloromethane can be used as the solvent. The compound of formula (2) can be prepared in the solvent, to which the compound of formula R¹—SO₂Hal can be added.

The isolation and cleaning of the compound of the invention can occur by customary means. To this end, for example, the solvent can be removed under reduced pressure and the raw product can be chromatographically cleaned on silica gel, for example.

Beginning with thymidine, uridine or cytidine, the compound of formula (2) can be produced by completion of the intramolecular ether formation, introduction of the protective group R, and configuration reversal. These reactions are known to the person skilled in the art, i.e., he/she is familiar with the necessary reaction conditions, chemicals and equipment.

A synthesis path for the compound of the invention, beginning with thymidine, is described in summary form below, wherein the method of the invention constitutes the final step. The method can also be applied analogously for production of the compound of the invention beginning with uridine or cytidine.

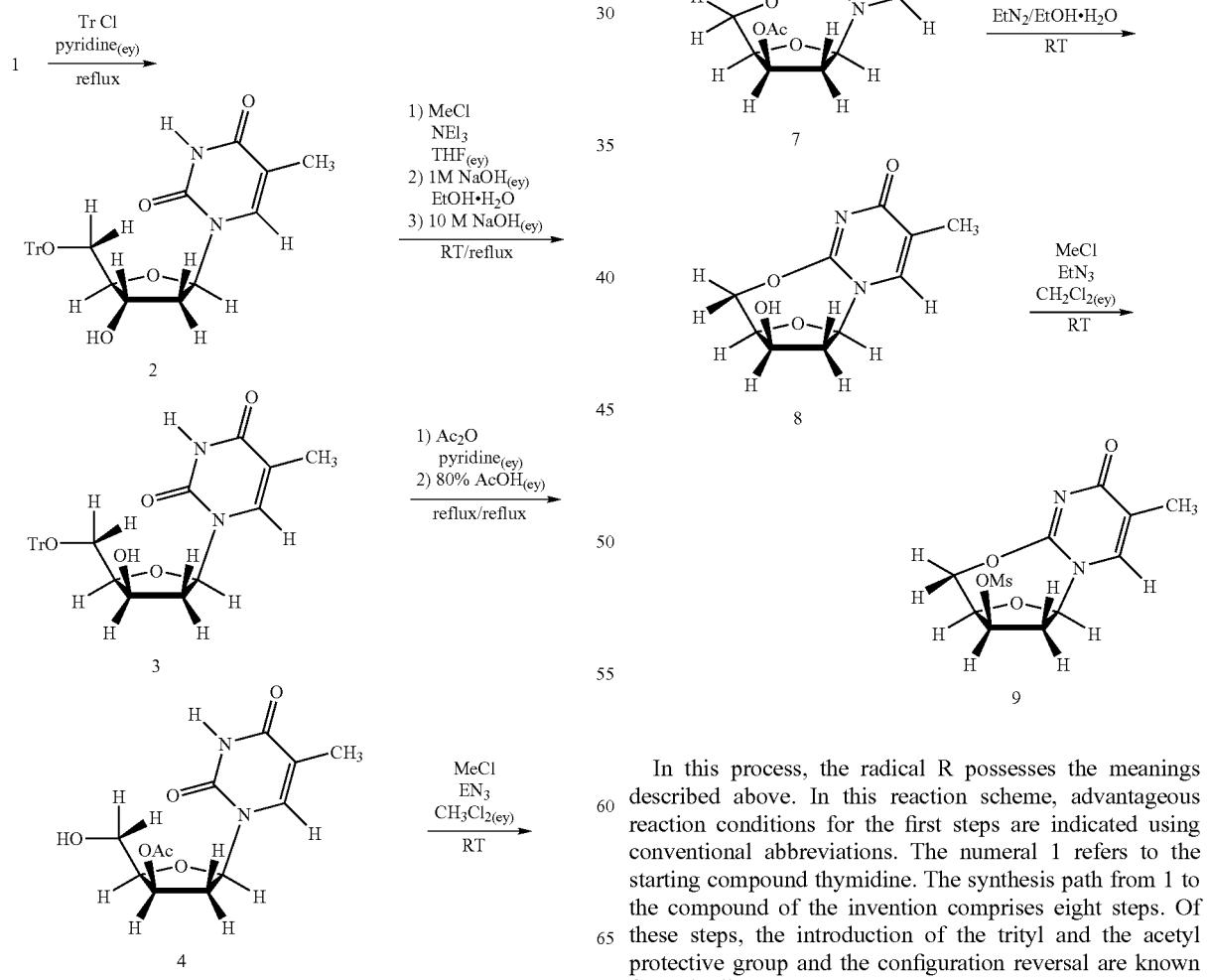

In this process, the radical R possesses the meanings described above. In this reaction scheme, advantageous reaction conditions for the first steps are indicated using conventional abbreviations. The numeral 1 refers to the starting compound thymidine. The synthesis path from 1 to the compound of the invention comprises eight steps. Of these steps, the introduction of the trityl and the acetyl protective group and the configuration reversal are known from the literature.

If commercially obtainable products are available that are listed in the above synthesis scheme as intermediate stages, the synthesis of the compound of the invention can, of course, begin with the commercial compounds.

The method of the invention has a number of advantages. For example, commercially available reagents that can be obtained quickly and cost-effectively are used as educts and/or solvents. In addition, conventional laboratory practices are used, such as conversion at room temperature, performing reactions with conventional stirrers, the use of inert gas, and chromatographic methods for isolating and cleaning products. The reaction temperature in the method of the invention is low, so that complex heating devices are not necessary. The solvents used in the method of the invention are generally low boiling and can thus be easily removed. Furthermore, the method of the invention allows for the use of solvents, such as acetonitrile, which are not as disturbing to separation by means of HPLC as DMSO. The method of the invention can be automated so that, for reasons of radiation protection, it is advantageous that the radiation load and contamination of human beings be kept as low as possible. Beginning with the compounds of the invention produced by means of the method of the invention, compounds marked with a positron-emitting radionuclide used in positron emission tomography, such as [$^{18}$F]FLT, can be produced that are obtainable in high yields and at a high degree of purity. In spite of the initial apparent complexity of the synthesis path, the individual steps can be quickly executed and produce good yields. The method of the invention offers a synthesis that is competitive with other methods in terms of the yield and purity of [$^{18}$F]FLT, for example, and is superior with regard to the development of toxic hydrolysis products.

The subject matter of this invention is also the use of the compound of the invention for inserting a nucleophile at the 3' position. Nucleophiles are "nucleus-seeking" particles, such as anions, carbanions or Lewis bases, which attack an electrophilic compound. These nucleophiles can be positron-emitting radionuclides. $^{18}$F is an example of a nucleophile. To illustrate this insertion, the production of [$^{18}$F]FLT is described below. This information also enables the person skilled in the art to insert other nucleophiles into the compound of the invention.

During the production of [$^{18}$F]FLT, the radical R is substituted by $^{18}$F in a compound of the invention, and a configuration reversal occurs in the process. Then the anhydro structure is hydrolyzed. Because there are no protective groups in the compounds of the invention, due to intramolecular cyclization, simple alkaline hydrolysis of the marked intermediate compound in a homogeneous solution into the desired product, [$^{18}$F]FLT, is possible without toxic protective group hydrolysates being split off. The hydrolysis can be acidic or alkaline, using, for example, sodium hydroxide solution or hydrochloric acid, which forms the non-toxic sodium chloride (table salt) following neutralization, wherein the sodium chloride can be split off using the subsequent cleaning process, in which HPLC is employed, for example.

During the marking reaction, the compound of the invention can be converted with [$^{18}$F]FLT in an organic solvent, especially acetonitrile, in the presence of a base, such as potassium carbonate, and a macrocyclic neutral ligand, such as Kryptofix®222 by Merck, into the [$^{18}$F]FLT protected by the anhydro structure, which is hydrolyzed. The raw product [$^{18}$F]FLT can be chromatographically cleaned, e.g., with a cleaning cartridge and/or by means of HPLC (e.g., run agent: $H_2O$:ethanol=92.5:7.5, isocratic; column: Phenomenex LUNA 5µ250×4.6 mm).

The method of the invention makes it possible, in a surprisingly facile and rapid manner, under mild conditions, and with good yields and a high degree of purity, to insert nucleophiles and, in particular, to produce proliferation markers. This production process can be automated, i.e., a device can be constructed with which this method can be performed automatically. This is preferred, for reasons of radiation protection, because radiation load and contamination of human beings are low in a fully-automated process. Because the proliferation marker can be obtained at a high degree of purity if it is synthesized on the basis of the compound of the invention, it can be administered to the patient either immediately or without further complex cleaning steps, thereby eliminating the adverse effects of possible impurities on the patient. Because of the high yield at which the proliferation marker can be obtained, sufficient quantities of marker to examine several patients can be produced in a single radiosynthesis.

The following example illustrates the invention in greater detail, but without limiting it to the example.

EXAMPLE 1

Synthesis of the Compound of the Invention 1-(3'-O-mesyl-2,5'-anhydro-β-D-lyxofuranosyl)-thymine Experimental Part Material and Methods General Analytical Part Melting points are uncorrected (Büichi, Flawil, Swiss model "535"). The elementary analyses were completed at the Organic Chemistry Institute of the University of Heidelberg. Mass spectra (FAB) were recorded on a Jeol JMS-SX-102A. Nuclear resonance spectra ($^1$H-, $^{13}$C-NMR) were recorded on a Bruker AM-500 or a Bruker AC-250 spectrometer (reference substance: tetramethyl silane).

Chemicals and Equipment

Chemicals and solvents, including anhydrous chemicals and solvents, were procured from Aldrich® (Deisenhofen, Germany) or Merck® (Darmstadt, Germany). The solvents were p.a. quality and were used without further cleaning. The column chromatography was performed on silica gel 60 (230–400 mesh, Fluka®, Sigma-Aldrich®, Deisenhofen, Germany). The thin layer chromatography plates (Polygram® SIL G/UV254 nm) were procured from Macherey-Nagel (Dueren, Germany).

High Performance Liquid Chromatography

The semi-preparative cleaning of the raw product, [$^{18}$F] FLT, was done with HPLC using an RP C18 column ("LUNA" model (250×21 mm; 5 µ) by Phenomenex, (Torrance, Calif., USA). Conditions: isocratic; ethanol/water=7.5/92.5 (v/v); flow: 10 $^{ml}/_{min}$. An inline filter, model A-410 (2 µm) by Upchurch Scientific (Oak Harbor, USA), was used. Radioactivity detector: Beckman Coulter "model 170" (Fullerton, Calif., USA). The automated distribution onto the HPLC column was accomplished with a 6-way motor valve (Besta "model 7060L," Wilhelmsfeld, Germany).

Analytic HPLC components: Radioactivity detector: BIOSCAN type, flowcount A' with diode (Macarthur, N W, Washington, D.C.). Column: LUNA (250×4.6 mm, 5 µ;

C18); Phenomenex (Torrance, Calif., USA). Conditions: isocratic; ethanol/water=7.5/92.5 (v/v); flow: 1 $^{ml}/_{min}$.

Radioactivity Measurements:

Capintec Radioisotope Calibrator CRC-2N (Pittsburgh, Pa., USA)

The [$^{18}$F] fluoride was supplied by the Scanditronix "MC 32 MI" cyclotron at the German Cancer Research Center (DKFZ, Heidelberg, Germany) through an $^{18}$O(p, n) $^{18}$F reaction using an [$^{18}$O] water target. The [$^{18}$F] fluoride was split off with a CHROMAFIX®-30 PS-HCO$_3^-$ cartridge (Macherey-Nagel, Düren, Germany) and eluted with 0.2 ml 0.05 M K$_2$CO$_3$ solution as aqueous potassium [$^{18}$F] fluoride solution.

Synthesis of 5'-O-trityl thymidine (2)

Thymidine (1) (5.15 g; 21.26 mmol) is dissolved in 100 ml of dry pyridine and, under inert gas, stirred with trityl chloride (7.02 g; 25.18 mmol) for 30 minutes under reflux. The reaction mixture is carefully poured into 1.5 l of ice water and stirred for an additional 30 minutes. The resulting precipitate is suctioned off. Most of the residual moisture is removed by dual azeotropic drying with ethanol on a rotation evaporator. Then the solid material is dried under an oil pump vacuum.

The recrystallization out of a benzol/acetone mixture produces (2) at a yield of 8.60 g (17.75 mmol 83.5% of theory).

Analytical data for (2): mp. 133.0–136.9° C.; TLC ($V_{MeOH}$: $V_{CH2C12}$=1:19) $R_f$=0.29; $^1$H NMR (CDCl$_3$)=9.36 (s, 1H, N—H), 7.56 (q, $^4$J=1.1 Hz, 1H, G—H), 7.44–7.19 (m, 15H, Tr-H), 6.42 (dd, $^3J_{1'-H,2'-Hx}$=8.1 Hz, $^3J_{1'-H,2'-He}$=5.9 Hz, 1H, 1'-H), 4.62–4.51 (m, 1H, 3'-H), 4.07 (ddd, $^3J_{4'-H,5'-H}$=2.9 Hz, $^3J_{4'-H,5'-H}$=2.9 Hz, $^3J_{4'-H,3'-H}$=2.9 Hz, 1H, 4'-H), 3.45 (dd, $^2$J=10.3 Hz, $^3$J=2.9 Hz, 1H, 5'-H), 3.36 (dd, $^2$J=10.5 Hz, $^3$J=3.1 Hz, 1H, 5'-H), 3.07 (d, $^3$J=4.4 Hz, 1H, 3'-O—H), 2.44 (ddd, $^2$J=13.5 Hz, $^3J_{2'-He,1'-H}$=5.8 Hz, $^3J_{2'-He,3'-H}$=2.8 Hz, 1H, 2'-He), 2.29 (ddd, $^2$J=13.7 Hz, $^3J_{2'-Hx,1'-H}$=7.6 Hz, $^3J_{2'-Hx,3'-H}$=6.2 Hz, 1H, 2'-Hx), 1.47 (d, $^4$J=1.1 Hz, 3H, 5-CH$_3$); LRMS (FAB$^+$) calculated for: C$_{29}$H$_{28}$O$_5$N$_2$Na [M+Na]$^+$ 507, measured: 507, calculated for C$_{29}$H$_{29}$O$_5$N$_2$ [M+H]$^+$ 485, measured: 485, calculated for C$_{29}$H$_{28}$O$_5$N$_2$ [M]$^+$ 484, measured: 484.

Synthesis of 1-(5'-O-trityl-2-deoxy-β-D-lyxofuranosyl)-thymine (3)

5'-O-trityl thymidine (2) (31.65 g; 65.32 mmol) is dissolved in dry THF under inert gas and while stirring. Following cooling to −10° C., triethylamine (21.0 ml) is added followed by mesyl chloride (7.0 ml), in portions over a 5-minute period, and the mixture is stirred for an additional 30 min. while being cooled. Then 60 ml of water, 60 ml of ethanol and 100 ml of 1 M NaOH solution are added and the reaction mixture is stirred under reflux for 90 minutes. Then 100 ml of 10 M NaOH solution are added and the mixture is kept under reflux for an additional 45 min. The solvent is extracted and water is added to the residue. The aqueous phase is extracted twice with 400 ml of ethyl acetate and the organic phase is dried with magnesium sulfate. This results in a white precipitate which, following filtration, is reduced to slurry in dichloromethane/ethylacetate (vol. 1/1) and then re-filtered. The combined organic phases are concentrated, spread onto 30 g of silica gel, and chromatographed. Eluent: $V_{MeOH}$: $V_{CH2C12}$=1:19 with 0.1% triethylamine. Yield of (3): 20.0 g; (41.275 mmol; 63.2% of theory).

Analytic data for (3): mp. 246.0–248.0° C.; TLC ($V_{MeOH}$: $V_{CH2C12}$=1:19) $R_f$=0.33; $^1$H NMR (CDCl$_3$)=9.09 (s, b, 1H, N-H), 7.61 (q, $^4$J=0.8 Hz, 1H, 6-H), 7.51–7.20 (m, 15H, Tr-H), 6.18 (dd, $^3J_{1'-H,2'-Hx}$=8.3 Hz, $^3J_{1'-H,2'-He}$=2.3 Hz, 1H, 1'-H), 4.48–4.40 (m, 1H, 3'-H), 4.03 (ddd, $^3J_{4'-H,5'-H}$=5.3 Hz, $^3J_{4'-H,5'-H}$=5.3 Hz, $^3J_{4'-H,3'-H}$=3.2 Hz, 1H, 4'-H), 3.64 (dd, $^2$J=10.2 Hz, $^3$J=5.1 Hz, 1H, 5'-H), 3.49 (dd, $^2$J=10.2 Hz, $^3$J=5.5 Hz, 1H, 5'-H), 3.10 (s, b, 1H, 3'-O—H), 2.56 (ddd, $^2$J=14.9 Hz, $^3J_{2'-Hx,1'-H}$=8.4 Hz, $^3J_{2'-Hx,3'-H}$=5.4 Hz, 1H, 2'-Hx), 2.17 (dd, $^2$J=15.3 Hz, $^3J_{2'-He,1'-H}$=2.1 Hz, 1H, 2'-He), 1.76(d, $^4$J=1.3 Hz, 3H, 5-CH$_3$); LRMS (FAB$^+$) calculated for: C$_{29}$H$_{28}$O$_5$N$_2$Na [M+Na]$^+$ 507, measured:507, calculated for C$_{29}$H$_{29}$O$_5$N$_2$[M+H]$^+$ 485, measured: 485, calculated for C$_{29}$H$_{28}$O$_5$N$_2$[M]$^+$ 484, measured: 484.

Synthesis of 1-(3'-O-acetyl-2-deoxy-β-D-lyxofuranosyl)-thymine (4)

1-(5'-O-trityl-2-deoxy-β-D-lyxofuranosyl)-thymine (3) (19.5 g; 0.0402 mmol) is dissolved in 270 ml of dry pyridine under inert gas in a 1 l single-neck flask with a gas attachment. Under ice bath cooling, acetanhydride (44 ml; 47.52 g; 0.4655 mol; 11.5 eq.) is added through a dropping funnel and then kept at reflux for 30 min. Then 400 ml of 80% acetic acid are added and the mixture is heated under reflux for an additional 2 hours. The solvent is extracted on a rotation evaporator, and the solvent is absorbed into dichloromethane, spread onto silica gel, and cleaned by means of column chromatography. Eluent: $V_{CH2C12}$/$V_{MeOH}$=95/5

Following rotation of the applicable fractions, a slightly yellow, foamy solid material remains.

Yield of (4): 7.96 g; (28.00 mmol; 70% of theory).

Synthesis of 1-(3'-O-acetyl-5'-O-mesyl-2-deoxy-β-D-lyxofuranosyl)-thymine (5)

1-(3'-O-acetyl-2-deoxy-β-D-lyxofuranosyl)-thymine (4) (7.56 g; 26.5953 mmol) is dissolved under inert gas and ice bath cooling in 100 ml of anhydrous dichloromethane. Triethylamine (11.1 ml; 80.077 mmol) and then mesyl chloride (6.2 ml; 80.1047 mmol), in portions, are added and the mixture is stirred for one hour. The solvent is extracted and the residue is spread onto silica gel and cleaned by means of column chromatography.

Eluent: $V_{CH2C12}$/$V_{MeOH}$=95/5

Following rotation of the applicable fractions, a brown oil remains.

Yield of (5): 7.3 g; (18.52 mmol; 65.8% of theory).

Synthesis of 1-(3'-O-acetyl-5'-iodo-2-deoxy-β-D-lyxofuranosyl)-thymine (6)

1-(3'-O-acetyl-5'-O-mesyl-2-deoxy-β-D-yxofuranosyl)-thymine (5) (10.2 g; 28.155 mmol) is dissolved under inert gas into 180 ml of anhydrous acetone in a 100 ml, heated, pressure-resistant glass reactor. Sodium iodide (30.12 g; 200.947 mmol) is added and the closed reactor is heated to 110° C. for 8 hours. Silica gel is added to the resulting red-brown suspension, the solvent is extracted, and the residue is dried overnight in an oil pump vacuum. The subsequent column-chromatographic cleaning produced 7.3 g of a brownish oil. Eluent: $V_{CH2C12}$/$V_{MeOH}$=95/5.

Yield of (6): 7.3 g; (18.52 mmol; 65.8% of theory).

Synthesis of 1-(3'-O-acetyl-2,5'-anhydro-β-D-lyxo-furanosyl)-thymine (7)

1-(3'-O-acetyl-5'-iodo-2-deoxy-β-D-lyxofuranosyl)-thymine (6) (5.16 g; 13.09 mmol) is dissolved in 300 ml of anhydrous acetonitrile. Silver acetate (11.03 g; 66.08 mmol; 5 eq.) is heated in a 500 ml single-neck flask with gas attachment, and the 1-(3'-O-acetyl-5'-iodo-2-deoxy-β-D-lyxofuranosyl)-thymine solution is added under inert gas. The suspension is kept at reflux for 5.5 hours. Then an additional 2.18 g of silver acetate are added and the mixture is boiled under reflux for an additional [1] hour. 15 g of silica gel are added to the reaction mixture, the solvent is extracted, and the residue is chromatographed. Eluent: $V_{CH2Cl2}/V_{MeOH}=85/15$.

Following removal of the solvent and drying under a high vacuum, 2.24 g of brown oil remains.

Yield of (7): 2.24 g; (8.41 mmol; 64.3% of theory).

Synthesis of 1-(2,5'-anhydro-β-D-lyxofuranosyl)-thymine (8)

1-(3'-O-acetyl-2,5'-anhydro-β-D-lyxofuranosyl)-thymine (7) (2.74 g; 10.29 mmol) is dissolved in a mixture of ethanol/water/triethylamine=4/2/1 and stirred at room temperature for 5 hours. The solvent is extracted on a rotation evaporator, and the residue is spread onto silica gel and cleaned by means of gas chromatography. Eluent: $V_{CH2Cl2}/V_{MeOH}=50/50$.

Following removal of the solvent and drying under a high vacuum, 1.7 g of beige, amorphous solid material remains.

Yield of (8): 1.7 g; (7.58 mmol; 73.7% of theory).

Synthesis of 1-(3'-O-mesyl-2,5-anhydro-β-D-lyxo-furanosyl)-thymine (9)

1-(2,5'-anhydro-β-D-lyxofuranosyl)-thymine (8) (1.64 g; 7.314 mmol) is dissolved under inert gas into dry dichloromethane in a heated 250 ml single-neck flask with gas attachment. Then, while stirring and cooling in an ice bath, triethylamine (5.1 ml; 3.7 g; 36.571 mmol), followed by portioned mesyl chloride (2.8 ml; 4.189 g; 36.571 mmol), are added and the mixture is allowed to reach room temperature. Following an hour of stirring at RT, an additional 1 ml of TEA and 0.5 ml of mesyl chloride are added and the mixture is stirred for 45 minutes. Following centrifugation of the solvent, the residue is spread onto silica gel and then chromatographed. Following removal of the solvent and drying under a high vacuum, 270.4 mg of white, crystalline solid material remain.

Yield of (9): 270.4 mg; (0.894 mmol; 12.2% of theory; MW=302.3 g).

The invention claimed is:
1. A compound of the following formula

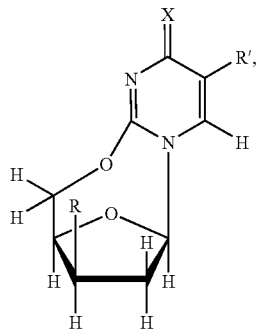

wherein R represents Br, I or $R^1$—$SO_3$, wherein $R^1$ is an unsubstituted or substituted $C_1$–$C_5$-alkyl group, or an unsubstituted or substituted phenyl group;

X is O or NR", wherein R" is a usual protective group for N; and

R' represents hydrogen, halogen, a substituted $C_1$–$C_7$-alkyl group, an unsubstituted $C_1$–$C_7$-alkyl group, a substituted $C_2$–$C_7$-alkenyl group, an unsubstituted $C_2$–$C_7$-alkenyl group, a substituted $C_2$–$C_7$-alkynyl group, or an unsubstituted $C_2$–$C_7$-alkynyl group;

wherein the moiety substituted on the $C_1$–$C_5$-alkyl group is an electron-withdrawing group, and wherein the moiety substituted on the phenyl group is a $C_1$–$C_5$-alkyl group or an electron-withdrawing group.

2. The compound of claim 1, wherein $R^1$—$SO_3$ comprises methane sulfonyl, 4-nitrophenylsulfonyl or p-toluene sulfonyl or trifluoromethane sulfonyl.

3. The compound of claim 1, wherein to compound is 1-(3'-O-mesyl-2,5'-anhydro-β-D-lyxofuranosyl)-thymine, 1-(3'-O-mesyl-2,5'-anhydro-β-D-lyxofuranosyl)-uridine or 1-(3'-O-mesyl-2,5'-anhydro-β-D-lyxofuranosyl)-cytidine.

4. A method for producing the compound of claim 1 comprising the step of introducing a radical R into a second compound having the following formula

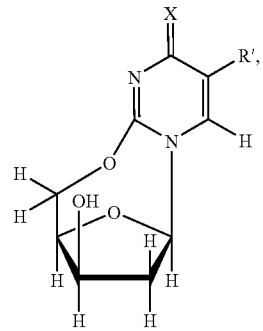

wherein R is Br, I, or a $R^1$—$SO_3$ group where $R^1$ is an unsubstituted or substituted $C_1$–$C_5$-alkyl group or an unsubstituted or substituted phenyl group;

X is O or a NR" group, where R" is a usual protective group for N; and

R' is hydrogen, a halogen, a substituted $C_1$–$C_7$-alkyl group, an unsubstituted $C_1$–$C_7$-alkyl group, a substituted $C_2$–$C_7$-alkenyl group, an unsubstituted $C_2$–$C_7$-alkenyl group, a substituted $C_2$–$C_7$-alkynyl group, or an unsubstituted $C_2$–$C_7$-alkynyl group;

wherein the moiety substituted on the $C_1$–$C_5$-alkyl group is an electron-withdrawing group, and wherein the moiety substituted on the phenyl group is a $C_1$–$C_5$-alkyl group or an electron-withdrawing group.

5. The method of claim 4 wherein the $R^1$—$SO_3$ group comprises methane sulfonyl, 4-nitrophenylsulfonyl, p-toluene sulfonyl, or trifluoromethane sulfonyl.

6. The method of claim 4 wherein the introducing step comprises the reaction of the second compound with a third compound having the formula $R^1$—$SO_2$Hal where $R^1$ is an unsubstituted or substituted $C_1$–$C_5$-alkyl group or an unsubstituted or substituted phenyl group; and Hal is halogen.

7. The method of claim 4 wherein Hal is chloride.

8. A method of making 3'-[$^{18}$F] fluoro-3'-deoxythymidine comprising the step of inserting a nucleophile at the 3' position of the compound of claim 1.

9. The method of claim 8 wherein the nucleophile is $^{18}$F.

* * * * *